United States Patent
Rosenblood

(10) Patent No.: US 7,523,044 B2
(45) Date of Patent: Apr. 21, 2009

(54) SYSTEM AND METHOD FOR PROVIDING CUSTOM FABRICATED PRODUCTS AND CATERED DENTAL REFERRALS FROM A RETAIL SITE

(75) Inventor: Kenneth Rosenblood, Los Angeles, CA (US)

(73) Assignee: Discus Dental, LLC, Culver City, CA (US)

( * ) Notice: Subject to any disclaimer, the term of this patent is extended or adjusted under 35 U.S.C. 154(b) by 233 days.

(21) Appl. No.: 11/074,430

(22) Filed: Mar. 7, 2005

(65) Prior Publication Data
US 2005/0203774 A1    Sep. 15, 2005

Related U.S. Application Data

(60) Provisional application No. 60/550,685, filed on Mar. 5, 2004, provisional application No. 60/553,575, filed on Mar. 16, 2004.

(51) Int. Cl.
G06Q 10/00    (2006.01)

(52) U.S. Cl. ........................ 705/2; 705/1; 705/3; 705/4; 705/26; 705/27; 725/105; 348/211.3; 348/E7.082

(58) Field of Classification Search ................. 705/1, 705/2, 3, 4, 26, 27; 725/105; 348/211.3, 348/E7.082
See application file for complete search history.

(56) References Cited

U.S. PATENT DOCUMENTS 7,174,308 B2 * 2/2007 Bergman et al. .............. 705/26

2003/0135865 A1 * 7/2003 Jung .......................... 725/105
2004/0122716 A1 * 6/2004 Yogesan ........................ 705/2
2005/0084826 A1    4/2005 Pilaro et al.

FOREIGN PATENT DOCUMENTS

JP    2002-083060 A    *    3/2002

OTHER PUBLICATIONS

International Search Report and Written Opinion dated Jan. 29, 2007, for PCT/US2005/07620, 6 pgs.
Translation of Japanese Patent Abstract published Mar. 22, 2002 for, 12 pgs.

* cited by examiner

Primary Examiner—Yogesh C Garg
(74) Attorney, Agent, or Firm—Christie, Parker & Hale, LLP

(57) ABSTRACT

A system and method for providing a consumer with dental services and products from a retail location, such as, for example, a local shopping mall. The dental service or product may include a teeth whitening product or service. The retail location is operated by a registered dental assistant or hygienist under supervision of a licensed off-site dentist. The dental assistant or hygienist uses an intra-oral camera and/or x-ray machine to take images of the customer's teeth and/or mouth. The images are transmitted to the off-site dentist over a data communications network. The off-site dentist evaluates the images and approves or denies a request for a particular dental service or product. If approved, the product or service is dispensed from the retail location. The off-site dentist may also recommend that the customer see a specialist. In this case, a referral to a specialist in the customer's area is made. An initial consultation with the specialist may also be conducted from the retail site, via video-conferencing technology.

29 Claims, 5 Drawing Sheets

SYSTEM AND METHOD FOR PROVIDING CUSTOM FABRICATED PRODUCTS AND CATERED DENTAL REFERRALS FROM A RETAIL SITE

CROSS-REFERENCE TO RELATED APPLICATIONS

This application claims the benefit of U.S. Provisional Application No. 60/550,685, filed on Mar. 5, 2004 and U.S. Provisional Application No. 60/553,575, filed on Mar. 16, 2004, the content of both of which are incorporated herein by reference.

BACKGROUND OF THE INVENTION

Better and easier accessible oral care in general can improve people's health. Proper guidance from a dentist can lead to proper dental hygiene, which can in turn help to prevent a variety of dental problems, such as tooth decay and root canal procedures. Whiter teeth can also make people feel better. Unfortunately, most people associate a visit to the dentist with unpleasantness, in addition to the inconvenience and the time associated with the visit. Even professional tooth whitening done in a dentist's office, though not necessarily associated with unhealthy teeth, can also be associated with the same unpleasant feelings. In addition, a patient must generally visit the dentist twice to receive a custom fitted whitening tray and gel: the first visit to take an impression of the patient's teeth, which is generally not done by the dentist, but by a licensed dental assistant or hygienist; and the second visit just to pick-up the finished whitening tray and the accompanying gel. Thus, having professional tooth whitening via a dentist is inconvenient. Furthermore, surveys show that only about 48% of the U.S population visits the dentist on a regular basis. Thus, a majority of the population has not been exposed to the benefits of professional, custom fabricated tooth whitening trays. According to this statistics, dentists are also missing out in the opportunity of serving this segment of the market.

Recently, custom fabricated tooth whitening systems have become available to the consumer through two alternative outlets beyond the dental office. A first outlet is in the form of mall kiosks or carts. These carts, however, have serious credibility issues in that the consumers are asked to take their own impressions in a questionable environment, such as, for example, a thoroughfare of a mall, with no dental professional on-site.

A second outlet is the Internet. Web sites exist that provide to a purchasing consumer a loaded impression tray that is used by the consumer to take his or her own impression, return it to the operator of the site, and then receive a custom tray with the whitening product. The web-based alternative may solve the visits to the dental office, but has added shortcomings, one of them being that the consumers generally have to take their own impressions, and another being that the consumers must generally wait for weeks before the finalized trays are received.

Over-the-counter whitening products can be another alternative to custom fabricated whitening trays. These products, however, have numerous shortcomings. Some consumers may not be able wear an over-the-counter whitening product due to involuntary tongue thrusting when the product is applied. These products, even after years of perfection, may still not be as effective as the whitening gels provided by dentists.

SUMMARY OF THE INVENTION

The present invention relates to a system and method for providing professional oral care that is, on the one hand, credible, easily accessible, and comfortable for the consumer, who may belong to the portion of the population who would normally visit a dentist regularly, who would normally not visit a dentist as often as he/she ought to, or who would normally not visit a dentist, and on the other hand, added business for a dentist to reach the portion of the population who would normally not visit a dentist's office, without the dentist having to leave his or her office.

According to one embodiment, the invention is directed to a computer-implemented method for providing a dental-related product or service from a retail location, such as, for example, a shopping mall. The method includes receiving from a requesting computer over a data communications network, a dental-related image taken at the retail location. A dental professional is identified in response to receipt of the dental-related image and the image forwarded to the identified dental professional over the data communications network. The dental professional reviews the dental-related image, along with any other relevant information, existing or acquired at the retail location, if any, and transmits an approval or denial message over the data communications network. The approval or denial message is then forwarded to the requesting computer.

According to one embodiment of the invention, the dental professional transmitting the approval or denial message is a licensed dentist who may legally approve or deny requested dental products or services, such as, for example, professional, custom fabricated tooth whitening trays and other custom fabricated products, oral health care products including products for prescribed protocols, and qualified referrals to local dentists.

According to one embodiment of the invention, the dental-related product or service is dispensed to the customer in response to an approval message.

According to another embodiment of the invention, information on the dental-related product or service requested by a customer is received from the requesting computer over the data communications network.

According to a further embodiment of the invention, a central database is searched for information on a referral doctor, and the information is transmitted to the requesting computer.

According to another embodiment, the present invention is directed to a computer-implemented method for providing a dental-related product or service from a retail location where the method includes taking, from the retail location, an image of a customer's teeth. The image is transmitted to a computer over a data communications network, and the computer forwards the image to a dental professional. The dental professional reviews the dental-related image, along with any other relevant information, existing or acquired at the retail location, if any, and transmits an approval or denial message over the data communications network. The dental-related product or service is then dispensed from the retail location in response to receipt of the approval message.

According to another embodiment, the present invention is directed to a system for dispensing dental-related products or services. The system includes a retail computer, a doctor computer, and a server coupled to the retail and doctor computers. The retail computer transmits a dental-related image taken at the retail site. The doctor computer is accessible by a dental professional, and receives the dental-related image. The doctor computer further transmits an approval or denial message in response to review of the dental-related image, along with any other relevant information, existing or acquired at the retail location, if any, by the dental professional. The server receives the dental-related image from the retail computer, identifies a dental professional in response, and forwards the dental-related image, along with any other relevant information, existing or acquired at the retail location, if any, to the doctor computer. The server also receives the approval or denial message transmitted by the doctor computer and forwards the approval or denial message to the retail computer.

It should be appreciated that the retail site is aimed at providing a credible, comfortable, accessible and fun environment where consumers can address some of their oral health care needs more frequently under one roof, without having the inconvenience of going to a dentist's office. It should also be appreciated that the retail site allows a dental professional to obtain patient referrals to visit their offices. Furthermore, the retail site allows a dental professional to provide dental care to patients who would not have visited a dental office, without leaving his/her own dental office. In addition, the retail site allows a dental professional to provide preparatory or necessary preliminary work to a patient before the patient visits the dental office.

DETAILED DESCRIPTION

Figure 1:
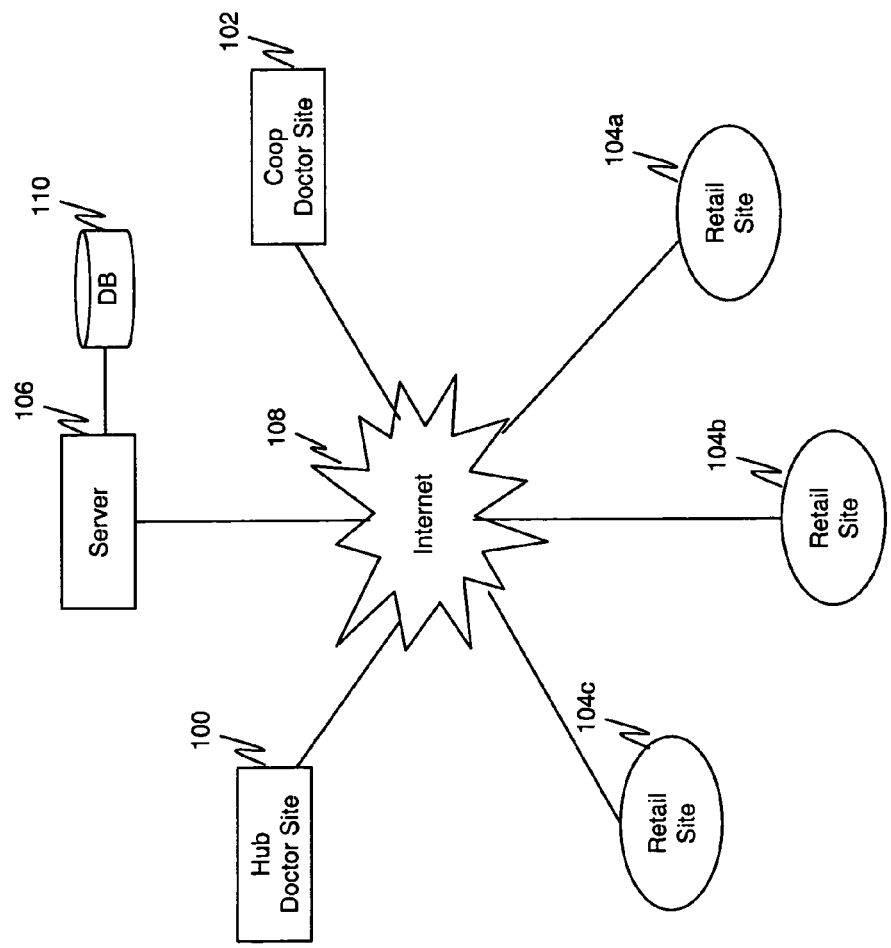
FIG. 1 is a schematic block diagram of a network system for providing custom fabricated products and catered dentist referrals from a retail site according to one embodiment of the invention.

The detailed description set forth below is intended as a description of a presently preferred method or device provided in accordance with aspects of the present invention, and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, preferred methods, devices, and materials are now described.

One embodiment of the present invention presents to the consumer the ability to purchase a custom fabricated product in a relatively short amount of time, at a relatively affordable price, from a credible, dental professional located at a convenient location. In one exemplary embodiment, instead of going to a dentist's office to get his or her teeth whitened, the consumer need only take a trip to his or her local mall where a dental professional at a retail site takes an impression of the consumer's teeth in a credible, comfortable, and fun environment. A custom-fitted whitening tray is then generated in a reasonable amount of time, for example, in one hour or less, ready for the consumer to use on the same day with a professional-strength whitening gel. During the time when the tray is being prepared, the consumer even has the option of either waiting for it in the store, going shopping in the mall, or shopping for other dental care products in the dental retail site.

Although custom-fitted whitening trays are used as an example, a person of skill in the art should recognize that other custom fabricated products may also be generated from the retail site, such as, for example, bruxing/grinding plates, athletic mouth guards, snore guards, tension suppression devices, orthodontic devices, such as braces and others, and the like. In addition, the customer may also receive routine services such as teeth cleaning, X-rays, other preparatory procedure such as preliminary examination for an oral procedure; receive or purchase oral health care products including dental care products or prescribed protocols; and receive qualified referrals to local dentists, who may be receiving dental information of the customer, online, without having to leave his or her own dental office.

As an exemplary illustration of the operation of the retail site, a consumer visits a store located in a local mall to purchase a custom-fabricated product, receive evaluations from an off-site dentist, receive dental care products and protocols for prescribed treatments, receive referrals to specialists with skills to address existing dental problems or aesthetic wants, or simply browse the store for information on oral health care and purchase related products.

Upon entry to the store, the consumer may be greeted by a staff member who may identify the purpose of the visit. If the consumer is to purchase a custom-fabricated product or desires an evaluation from an off-site dentist, the staff member directs the consumer to a section of the store where an intra-oral camera is operated by a registered dental assistant (RDA) and/or registered dental hygienist (RDH) to transmit images of the consumer's teeth or mouth to the dentist on-call. The dentist evaluates the dental problems and aesthetic wants, revealed by the transmitted images. The evaluation may be conducted, for example, in real time via video-conferencing technology well known in the art.

Based on the evaluation, the dentist may approve or deny a custom-fabricated product for the consumer. If no custom-fabricated product is desired, the dentist may approve or deny a particular treatment to be conducted at the retail site by the RDA or RDH. Such a treatment may be, for example, chair-side bleaching where a whitening bleach agent is painted onto the teeth and a special light is used at various intervals to help activate the tooth whitening agent, such as, for example, a Zoom! tooth whitening procedure, marketed by Discus Dental, Incorporated, of Culver City, Calif. The treatment may also include laser bleaching.

If a custom fabricated product is approved, the RDA or RDH takes an impression of the consumer's teeth and forwards it to an in-store or nearby lab to generate the custom product. The consumer may wait for the product in the retail store, browsing through information provided by the various interactive panels or products offered by the store. The consumer may also leave and go shopping in the mall, and return later in the day when the product is estimated to be ready, as noted above. The custom-fabricated product may then be used by the consumer at home, or used at the retail site for a particular onsite treatment.

The dentist evaluating the dental images may inform the consumer of potential problems or aesthetic wants that the consumer may want to address, such as for example, an incipient lesion, a detected cavity, broken tooth, abnormal bite, and the like. The dentist may then recommend the consumer additional custom fabricated products, or, if a specialist is desirable, to a specialist in the consumer's area. If a specialist is recommended, the consumer may then conduct a live, initial consultation with the recommended specialist via video conference. The specialist may provide information about a potential treatment, the timeframe and cost of such treatment, and even book the consumer for a second, in-office visit.

FIG. 1 is a schematic block diagram of a network system for providing custom fabricated products and catered dentist referrals from a retail site according to one embodiment of the invention. According to the illustrated embodiment, the system includes one or more hub doctor sites 100, cooperative doctor sites 102, and retail sites 104a-104c (collectively referenced as 104), communicating with a central server 106 over a data communications network 108 such as, for example, a local area network, a wide area network, the Internet, and the like. Each site may connect to the network using conventional wired or wireless connection mechanisms such as for example, cable connections, DSL connections, or any other high speed connections known in the art.

The server is coupled to a central database 110 storing information on registered and hub doctors and cooperative doctors. Such information may relate to the doctors' specialties, geographic information, IP addresses, contact information, insurance information, languages spoken, and the like. The central database also stores patient files and other information that may be accessed by the retail sites for generating the custom fabricated products and making catered dentist referrals.

According to one embodiment of the invention, a hub doctor operating the hub doctor site 100 provides remote general supervision of RDAs or RDHs employed at the retail sites 104. With this general supervision, the RDAs or RDHs may operate intra-oral cameras to take images of the consumer's teeth and mouth, take impressions, and perform other tasks that may be performed at a dentist's office.

The retail site 104 may also be equipped with instrumentation similar to those in a dental office that is operated by an RDA and/or RDH, with additional equipment for imaging and digital transmission, so that a dentist, in his or her office can view transmitted files and prescribe treatments or preparatory procedure without having the consumer visit the dental office.

Figure 2:
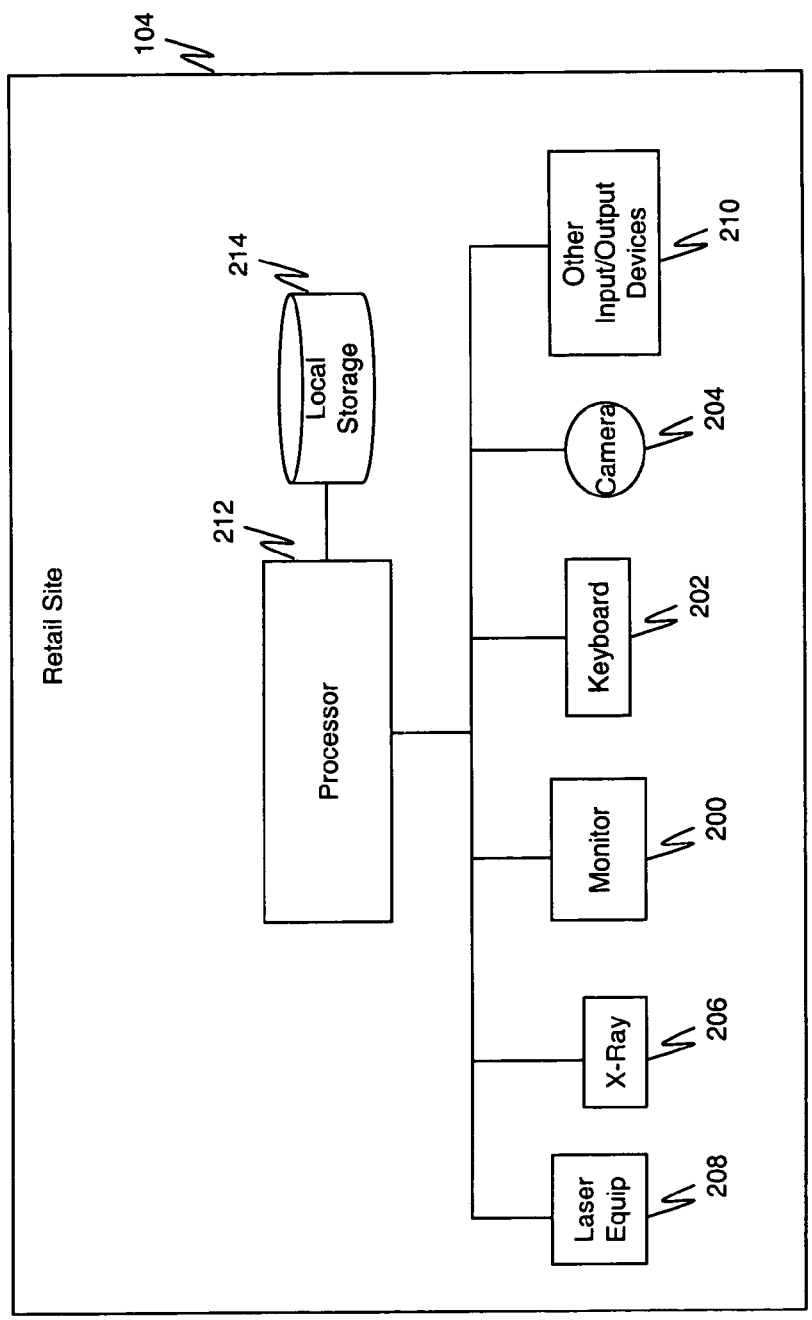
FIG. 2 is a more detailed diagram of a retail site according to one embodiment of the invention.

FIG. 2 is a more detailed diagram of the retail site 104 including one or more retail computers according to one embodiment of the invention. The retail site 104 includes, according to this illustrated embodiment, one or more monitors 200, keyboards 202, cameras 204 (e.g. intra-oral cameras, digital cameras, video cameras, NetCams, etc.), digital x-ray machines 206, laser fluorescence equipment 208 (e.g. for electronic caries detection), and other input/output devices 210, coupled to at least one processor 212 either directly or over a wired or wireless local area network, personal area network, or the like. The processor 212 is configured with all hardware and software for transmitting and receiving data to and from the various devices to which it is connected. The processor is also configured with all hardware and software for transmitting still and/or moving images captured by the camera over the data communications network, including all software and hardware for streaming video files and conducting video conferencing with a hub or cooperative doctor. The communication lines may also have voice over data capabilities for live interactions.

According to one embodiment of the invention, the processor 212 hosts a web browsing software for accessing web pages provided by the server 106. The processor 212 is also coupled to a local data store 214 storing patient information and/or image data locally at the retail site.

Figure 3:
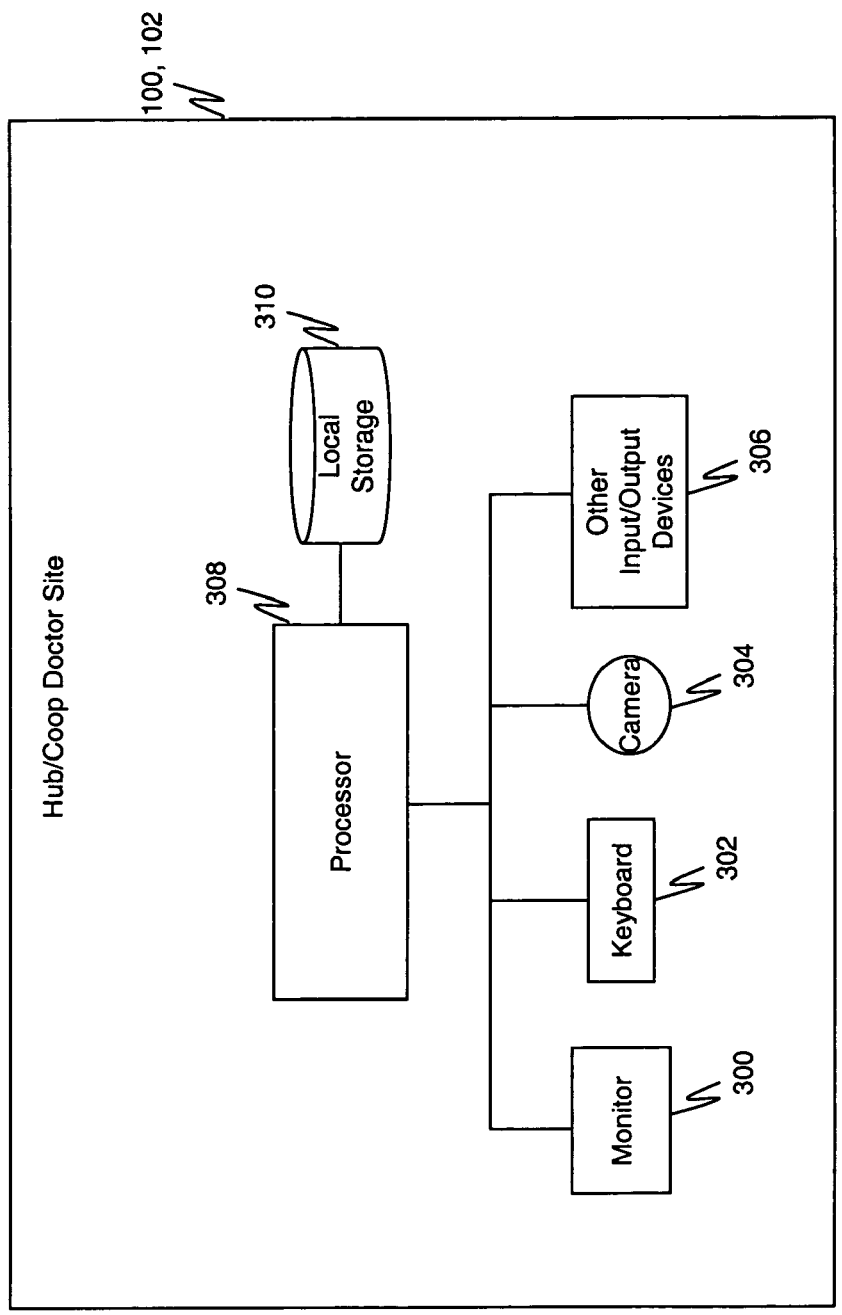
FIG. 3 is a more detailed diagram of a hub or cooperative doctor site according to one embodiment of the invention.

FIG. 3 is a more detailed diagram of the hub or cooperative doctor site 100, 102 (collectively referenced as the doctor site) including one or more doctor computers according to one embodiment of the invention. According to one embodiment, the doctor site is operated by a dentist who is licensed to practice dentistry in one or more retail site locations.

The doctor site includes, according to this illustrated embodiment, one or more monitors 300, keyboards 302, cameras 304 (e.g. digital cameras, video cameras, NetCams, etc.), and other input/output devices 306 coupled to at least one processor 308 either directly or over a wired or wireless local area network, personal area network, or the like. The processor 308 is configured with all hardware and software for transmitting and receiving data to and from the various devices to which it is connected. The processor is also configured with all hardware and software for transmitting still and/or moving images captured by the camera over the wide area network, such as, for example, software and hardware for conducting video conferencing with the retail site 104, and the like.

According to one embodiment of the invention, the processor 308 hosts a web browsing software for accessing web pages provided by the server 106. The processor is also coupled to a local data store 310 storing patient information and/or image data locally at the doctor site.

Figure 4:
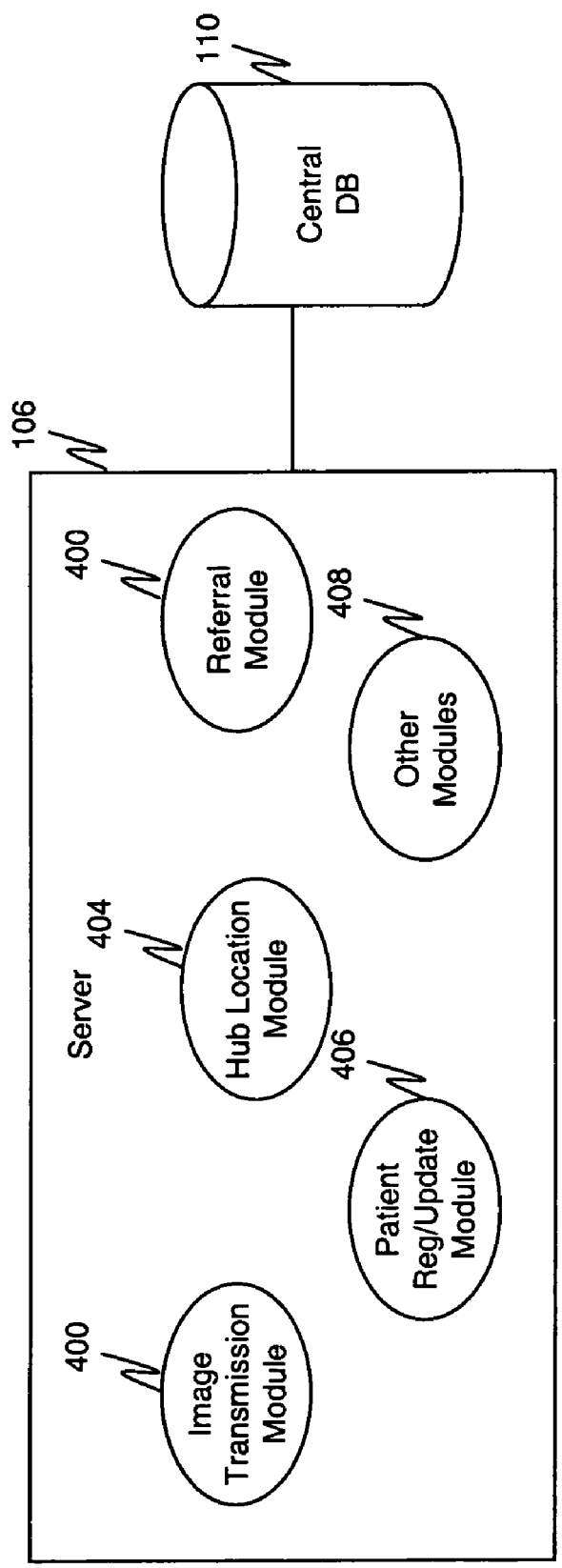
FIG. 4 is a more detailed diagram of a server according to one embodiment of the invention.

FIG. 4 is a more detailed diagram of the server 106 according to one embodiment of the invention. According to the illustrated embodiment, the server hosts a web site that is accessed by the doctor and retail sites 100, 102, 104 to communicate with each other and provide the user with the custom fabricated products and referrals from the retail site. Voice over data capabilities may also be included for live interactions between the retail site 104 and the doctor sites 100, 102. In this regard, the server includes an image transmission module 400, referral module 402, hub location module 404, and patient registration/update module 406. The server may also include other types of software and/or hardware modules 408 as will be appreciated by a person of skill in the art, such as, for example, a video conferencing module.

The image transmission module 400 is configured to transmit still and/or video images captured by intra-oral and other types of cameras, x-ray machines, and the like, located at the retail or doctor sites. Voice data may also accompany the transmitted images. The referral module 402 is configured to search the central database 110 for information on registered cooperative doctors to whom referrals may be made based on the specialty selected by the hub doctor and other types of criteria programmed into the module. The hub location module 404 is configured to identify a hub doctor site 100 that is associated with a particular retail site 104. The patient registration/update module 406 creates or updates patient record files stored in the central database 110 based on information transmitted by the doctor or retail sites 100, 102, 104.

In addition, cooperative doctors may be networked together from anywhere in the forty-eight states. A customer may be referred or to pick up dental supplies anywhere within the network. For example, a customer on vacation, or on a visit to a friend or family, can also visit a retail site to take care of their dental care needs.

Figure 5:
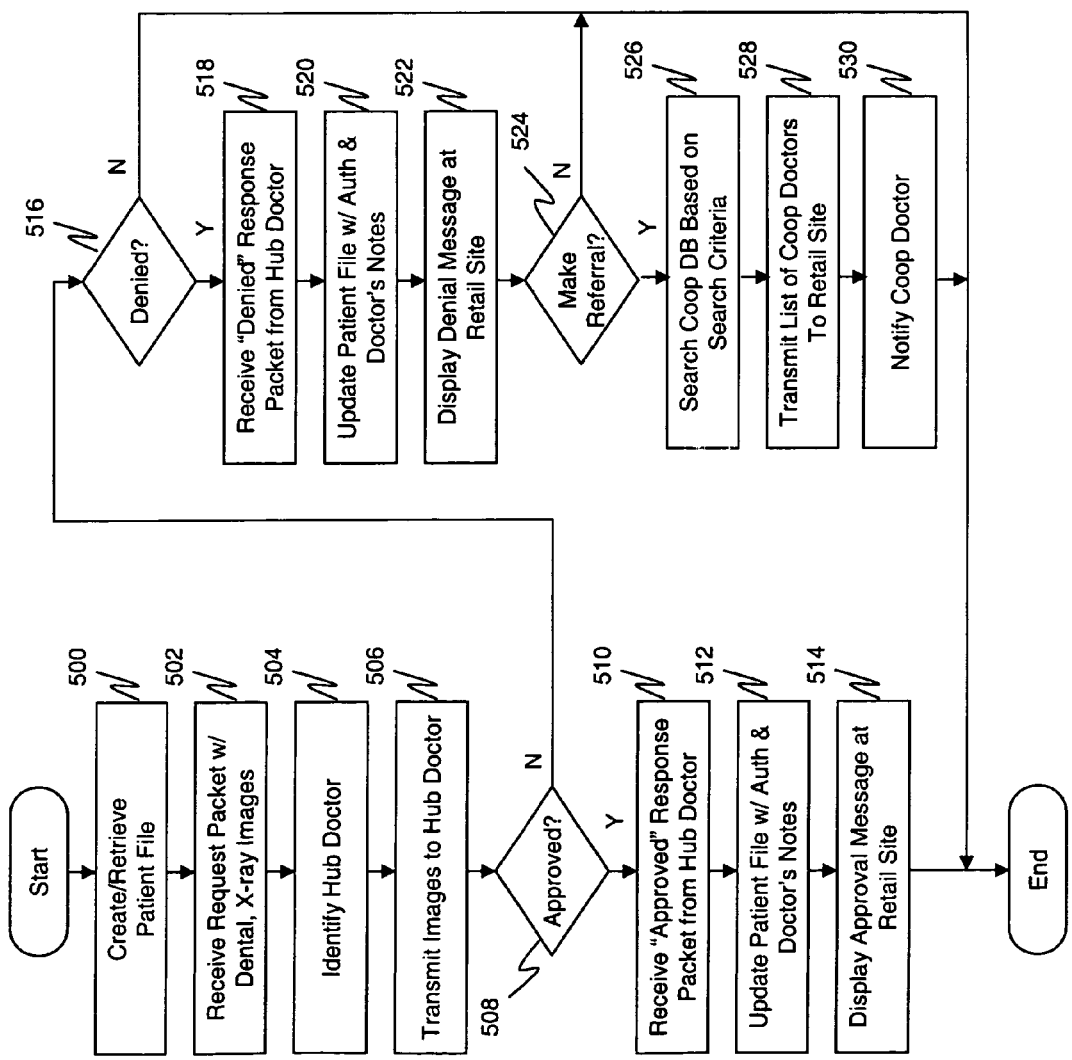
FIG. 5 is a flow diagram of a process engaged by the server of FIG. 4 for allowing a patient to obtain a custom fabricated product and/or a doctor referral according to one embodiment of the invention.

FIG. 5 is a flow diagram of a process engaged by the server for allowing a patient to obtain a custom fabricated product and/or doctor referral according to one embodiment of the invention. An employee at a retail site accesses the server 106 to request a new patient file or to retrieve an exiting patient file. The request is handled by the patient registration/update module 406 which, in step 500, provides the requested patient file or a web page with fields to be completed to generate a new patient record. The fields may prompt for the patient's name, address, age, gender, native language, insurance information, basic medical and dental health information, and the like. The information is then stored in the patient's record in the central database 110. The information may also be stored locally at the retail site 104.

An RDA or RDH then operates the camera 204 to generate dental images of the patient's teeth and mouth. The RDA or RDH may also operate the digital x-ray 206 to take digital x-ray images of the teeth. The dental and/or x-ray images may be compressed according to any of the well-known compression technologies, and transmitted to the server 106 in a form of a request packet. According to one embodiment of the invention, the request packet may include a request number, include information on a particular service/product requested by the patient (e.g. tooth whitening), and information on the patient (e.g. patient file number) for which the request is being made.

The patient registration/update module 406 receives the request packet in step 502, retrieves the dental images, and stores the images in the central database 110 in association with the patient file. The images may also be stored locally at the retail site in the local data store 214.

In step 504, the server invokes the hub location module 404 to identify a hub doctor that is to evaluate the request. The determination may be made, for example, based on a source IP address of the request packet, or based on the geographic location of the retail site 104. In another embodiment of the invention, a cooperative doctor may be selected to take the role of the hub doctor.

In one embodiment of the invention, the hub doctor is on call during normal hours of the retail site operation, waiting to review images transmitted in the request packet by the retail sites. In this regard, the image transmission module 400 posts a link or an icon on the hub doctor's web page to alert the doctor that dental images are pending his or her review. According to another embodiment of the invention, the icon or link, or the actual images along with all or a portion of the information contained in the request packet, is transmitted to the doctor in the form of an e-mail, instant message, page alert, or the like. Other visual or audio notifications may also be transmitted to the doctor's telephone, cellular phone, computer, pager, personal digital assistant (PDA), or other portable or non-portable device, to alert the doctor of the pending images.

According to one embodiment of the invention, the hub doctor views the images transmitted by the retail site by selecting the icon or link provided by the server. The image transmission module 400 responds to the selection by forwarding, in step 506, the request containing the dental images to the hub doctor. According to one embodiment of the invention, the dental images are transmitted over the data communications network 108 as streaming or non-streaming video. All or portion of the request including information of the particular service/product requested by the patient, and/or a portion of the patient information stored in the patient file may also be transmitted to the hub doctor.

According to another embodiment of the invention, the images captured by the camera 204 are transmitted in a live broadcast as part of a video-conference between the retail site 104 and the hub doctor at the hub doctor site 100. This may allow the hub doctor to interact with the RDA or RDH in real-time while conducting the examination of the patient's teeth. For example, the doctor may provide instructions to the RDA or RDH as to the positioning of the intra-oral camera, request verbal information about the patient's teeth based on the RDA or RDH's observations that may not be captured by the camera, and the like.

The hub doctor examines the dental images as well as any x-ray images and associated patient information for determining whether the patient is suitable to undergo the treatment that is requested. In the scenario where the treatment is tooth whitening, whether it be a nightguard bleaching process conducted at home via a custom-fitted whitening tray, or light activated or laser bleaching conducted at the retail site with or without a tray, the hub doctor may examine the dental images for exposed dentin, exposed roots, and/or other periodontal issues. The doctor may further enter comments and evaluation notes into the web page displaying the request, in association with the images that are being viewed.

According to one embodiment of the invention, if the doctor determines that further inspection of the tooth is necessary, he or she may transmit a command to this effect. For example, the doctor may request that x-rays be taken of the patient's teeth. The doctor may also request additional examination via the inter-oral camera. Such commands may be transmitted orally during a live video-conference with the retail site. Otherwise, the commands may be transmitted by selecting appropriate icons or menu items on the doctor's web page, by transmitting an instant message, or the like.

If the hub doctor approves the request for service or treatment, whether it be making a custom fabricated product and/or onsite treatment for the patient, as is determined in step 508, the doctor transmits an "approved" response to the retail site. This may be done, for example, by selecting an "approved" button on the displayed web page. Selection of the "approved" button causes the processor 308 at the hub doctor site 100 to generate and transmit the "approved" response packet to the server 106, along with any verbal or written comments or notes entered by the doctor. According to one embodiment of the invention, the "approved" response packet may identify the request to which the response is being made as well as information on the doctor and/or doctor site 100 submitting the response.

In step 510, the server 106 receives the "approved" response packet, and in step 512 updates the patient's record with the approval information and the doctor's comments and notes. The approval, comments, and notes may further be correlated with the particular dental images to which they relate.

In step 514, the server 106 transmits an "approved" message to the retail site for display on a display monitor. All or part of the notes and comments made by the hub doctor may also be displayed on the display monitor along with the approval message.

Display of the approval message causes the RDA or RDH to proceed with the making of the customized product and/or conducting an onsite treatment. This may be done, for example, by taking an impression of the patient's teeth and generating the customized product from the impression.

Depending on the type of custom-fitted product being fabricated and/or treatment to be rendered, the RDA or RDH may transmit additional information associated with the product and/or treatment for storing in the patient's record. For example, in the scenario where the consumer's teeth are to be whitened, the RDA or RDH may transmit to the server 106 information on the current shade of the patient's teeth. The server may then update the patient's record with the shade information.

According to one embodiment of the invention, either the server or the processor at the retail site is configured with software that generates an image of the patient's teeth before and after treatment using the custom fabricated product. In the tooth whitening example, an image of the patient's teeth with the current shade may be displayed with an image of what the patient's teeth is expected to look like after the whitening treatment has been completed.

After receipt of the doctor's approval for a particular custom fabricated product and/or treatment, the RDA or RDH proceeds to take steps for generating the product and/or rendering the treatment. For example, if the consumer desires a whitening tray for nightguard bleaching, the RDA or RDH takes an impression of the consumer's teeth for making a whitening tray either onsite or at a nearby lab. The whitening tray may then be dispensed with a whitening bleach solution to be used at the consumer's home.

If the consumer desires chairside bleaching, the RDA or RDH proceeds to paint a whitening bleach agent onto the consumer's teeth, and a special light is used at various intervals to help activate the tooth whitening agent. The chairside bleaching can utilize, for example, Zoom! Or ZOOM2 products and processes marketed by Discus Dental, Incorporated, of Culver City, Calif. The RDA or RDH may further operate a laser equipment for laser bleaching. According to one embodiment of the invention, the hub doctor may oversee an on-site treatment being rendered by the RDA or RDH via video conference. The doctor may also inspect a custom fabricated product for fit and the like, via video conference.

In the event, however, that the hub doctor does not approve the making of the custom-fitted product and/or treatment for the patient, as is determined in step 516, the doctor may enter the reasons for the denial in the comments or notes portion of the displayed web page. The doctor then transmits a "deny" response to the retail site. This may be done, for example, by selecting a "deny" button on the displayed web page. Selection of the "deny" button causes the processor 308 at the hub doctor site 100 to generate and transmit a "deny" response packet to the server 106 along with the reasons for denial and any other additional notes and comments entered by the doctor. According to one embodiment of the invention, the "deny" response packet may identify the request to which the response is being made as well as information on the doctor and/or doctor site 100 submitting the response.

In step 518, the server 106 receives the "deny" response packet, and in step 520 updates the patient's record with the denial information and the notes and comments.

In step 522, the server 106 transmits a "denied" message to the retail site for display on a display monitor. The reasons for denial as well other notes and comments made by the hub doctor may also be displayed on the display monitor along with the denial message.

According to one embodiment of the invention, if a denial is made for reasons that require attention by a specialist, the hub doctor may refer the patient to the appropriate specialist based on the evaluation of the dental images. This may be accomplished, for example, by selecting a specialty area equipped to handle the patient's particular dental issues from a pull-down list of specialties, and selecting a referral button. Dental specialists may include those practicing in the area of endodontics, periodontics, orthodontics, pedadontics, oral surgery, cosmetics, restoratives, and general practice.

In this regard, the server determines, in step 524, whether the hub doctor has requested a referral. Is the answer is YES, the server invokes the referral module 402 in step 526 for searching a database of registered cooperative doctors in the indicated specialty. In determining a list of the most suitable cooperative doctors to be referred to the patient, the referral module uses one or more fields in the patient's record as a search criteria for performing the search. For example, the doctors in the indicated specialty area may be selected based on the patient's zip code, native language, insurance information, and the like. The retrieved doctors may then be ranked according to a predetermined criteria, such as, for example, based on a distance to the patient's home.

In step 528, the server transmits a list of the identified doctors to the retail site for display on the display monitor. If the patient desires to talk to the referred specialist(s) on the spot, the referral module transmits a notification to the referred specialist(s). In another embodiment of the invention, the notification may be transmitted automatically in step 530 without requiring specific user consent.

According to one embodiment of the invention, if multiple doctors in a specialty area are retrieved by the referral module, the server contacts a first doctor on the list, and if a response is not received within a predetermined amount of time, transmits a notification to a second doctor on the list. This may continue until a doctor in the referral list responds. According to one embodiment of the invention, the hub doctor is notified if no doctor on the referral list responds. In the event of such an occurrence, the consumer has the choice of waiting while the server attempts to repeat the contacting process, or the consumer can leave behind a contact number at the retail location for a specialist to contact him/her.

The notification may be transmitted to the referral doctor's telephone, cellular phone, computer, pager, personal digital assistant (PDA), or the like. According to one embodiment of the invention, a link or an icon for accessing the patient's information and associated dental images may be transmitted with the notification.

According to one embodiment of the invention, either a responding cooperative doctor or the retail site initiates a video conference with the other to allow the patient to receive an initial, live consultation with the referred doctor, on the spot. The patient may also schedule a second office appointment during the video conference.

The referral service and live video-conferencing capabilities help overcome some of the multitude of challenges faced by traditional patient referral networks, such as, for example, the referred patient not being handled appropriately by front office staff, the patient not showing for an initial appointment, the patient's needs not being commensurate with the dentist's skill set, and the like. Because the appropriate specialist is selected by the hub doctor who understands the patient's needs, the patient is matched to a doctor who is deemed to be qualified to meet those needs. Furthermore, because the patient may see and speak directly to the referred doctor, the patient may have immediate peace-of-mind as to from whom they will be receiving their treatment.

According to one embodiment of the invention, the patient may also visit the retail site due to various types of dental problems such as, for example, crooked, missing, or chipped teeth. Like in the tooth whitening scenario, the RDA or RDH takes images of the patient's teeth and mouth using the intra-oral camera, and the images are transmitted to a hub doctor on-call. The hub doctor may review the images and approve a custom-fabricated product such as, for example, an invisible brace. The hub doctor may also select a specialist to whom the patient should be recommended. In either scenario, an image of the patient's current teeth with the crooked, missing, or chipped tooth may be generated besides another image reflecting how the patient's teeth would look with the problem corrected.

According to one embodiment of the invention, the retail site may also serve as a specialty shop for oral health care products. In this regard, the retail site may provide a comprehensive line of products researched and assembled by dental professionals, with a focus to create an optimal oral health care program for each and every customer visiting the retail site, which may range from an infant, to an elderly person, to even a customer with special needs. Exemplary products offered by the retail site may include toothpastes, breath control products, professional strength products previously only dispensed through a dentist or pharmacy, manual and electronic toothbrushes, oral irrigators, neutracueticals, lip balms, canker/cold sore remedies, and other preventative products, some of which may also be packaged for a prescribed protocol, for example, one that includes the use of a chlorhexadine rinse, a 5000 ppm fluoride tooth paste and a xylentol breath mint.

Because licensed hub doctors provide the general supervision of the retail sites, the sites may dispense prescription oral care products to the consumers.

The retail site may also provide a section dedicated to children's products. This section may feature oral care products for kids, as well as books, videos, and fun aids for assisting children with the overall care of their teeth. The retail site may even re-create the Tooth Fairy, and offer a unique product called Tooth Fairy Grams (gift certificates), allowing relatives such as grandparents to participate in the gift giving when their grandchildren loose their teeth According to one embodiment of the invention, the consumer's purchase history is maintained for each consumer in his or her record file. The consumer may be provided with a customer card which will allow the retrieval of such customer records to provide a personalized service to the customer.

According to one embodiment of the invention, the retail site also serves as an information center for oral-health related issues. One or more interactive panel displays strategically placed throughout the retail site may feature educational information about the store, products offered by the store, and oral health care information. The interactive displays may be informative, and aid the customer in purchasing the right product. The displays may further compliment the retail site's staff knowledge base. For example, the interactive displays may provide information from when to start brushing an infant's teeth, to geriatric oral care, to recommending a toothpaste for the chronic canker sore sufferer, and the like. The interactive displays may work in tandem with a highly professional, well trained, and knowledgeable sales force to provide the consumer with the appropriate oral health care information and products.

Although this invention has been described in certain specific embodiments, those skilled in the art will have no difficulty devising variations to the described embodiment which in no way depart from the scope and spirit of the present invention. For example, although the various modules described herein are described as being software modules implemented on one or more processors, a person of skill in the art should recognize that the modules may be implemented in hardware, firmware, or any combination of software, hardware or firmware. Furthermore, the steps described in the flow diagrams may be implemented in the indicated order, or in any other order recognized by a person of skill in the art.

Moreover, to those skilled in the various arts, the invention itself herein will suggest solutions to other tasks and adaptations for other applications. It is the applicants' intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive.

What is claimed is:

1. A computer-implemented method for providing a dental-related product or service from a retail location where a licensed dentist is not physically present, the method comprising:
   receiving from a requesting computer over a data communications network, a dental-related image of a customer taken by at least one staff member at the retail location and a request for a dental-related product or service;
   identifying the licensed dentist in response to receipt of at least the request;
   forwarding the dental-related image and the request to a doctor computer accessible by the identified dentist over the data communications network;
   receiving a message from the dentist over the data communications network approving or denying the request for the dental-related product or service, the message being transmitted in response to review of the dental-related image by the dentist;
   forwarding the message to the requesting computer, wherein the message is displayed on the requesting computer for prompting the at least one staff member at the retail location to dispense the dental-related product or service from the retail location if the message is a message approving the request for the dental-related product or service, and for prompting the at least one staff member at the retail location to not dispense the dental-related product or service from the retail location if the message is a message denying the request for the dental-related product or service;
   receiving from the doctor computer over the data communications network identification of a particular type of specialty for referring the customer;
   identifying a list of doctors associated with the identified specialty;
   transmitting by a server a first notification to at least one doctor in the list;
   determining by the server whether a predetermined amount of time has elapsed without a response to the first notification before transmitting a second notification; and
   automatically establishing a videoconference session between the requesting computer and a responsive doctor computer accessible by at least one of the doctors in the list.

2. The method of claim 1, wherein the dental-related product or service is a teeth whitening product or service.

3. The method of claim 1 further comprising:
   retrieving a file from a central database associated with the customer for whom the dental-related product or service is dispensed, and storing the dental-related image into the file.

4. The method of claim 1 further comprising:
   searching a central database for information on a referral doctor; and
   transmitting the information to the requesting computer.

5. The method of claim 1, wherein the retail location is in a shopping mall.

6. The method of claim 1, wherein the at least one staff member is a dental assistant.

7. The method of claim 1, wherein the dental-related image is a video image, and the method includes remotely monitoring via an established real-time video transfer session the dispensing of the dental-related product or service.

8. The method of claim 1 further comprising:
providing a plurality of available dental-related products or services, wherein the request for the dental-related product or service is a request for a particular one of the plurality of available dental-related products or services.

9. The method of claim 1, wherein the dental-related product or service is dispensed from the retail location without requiring the customer to visit a dental office to receive the dental-related product or service.

10. The method of claim 1, wherein the real-time video transfer session is a videoconferencing session including both video and audio data transfers.

11. The method of claim 1 further comprising:
establishing a real-time video transfer session between the requesting computer and the doctor computer; and
remotely conducting dental examination of the customer via the real-time video transfer session, wherein the message approving or denying the request for the dental-related product or service is in response to the remotely conducted dental examination.

12. The method of claim 11, wherein the remotely conducting the dental examination includes transmitting, during the real-time video transfer session, instructions to the requesting computer indicating a location of an image capture device for capturing one or more second dental-related images at the indicated location, the captured one or more dental-related images being transmitted to the doctor computer during the real-time video transfer session.

13. The method of claim 1 further comprising:
receiving comments from the doctor computer in response to review of the dental-related image by the dentist;
correlating the comments to the dental-related image; and
storing the dental-related image with the correlated comments in a central database.

14. The method of claim 1 further comprising:
storing the dental-related image in a central database;
forwarding to the doctor computer a notification message, the notification message including a link to the stored dental-related image; and
forwarding the dental-related image to the doctor computer in response to actuation of the link in the notification message.

15. The method of claim 1 further comprising:
establishing a real-time video transfer session between the requesting computer and the doctor computer in response to the message approving the request for the dental-related product or service.

16. A computer-implemented method for providing a dental-related product or service from a retail location where a licensed dentist is not physically present, the method comprising:
at the retail location, taking an image of a customer's teeth responsive to a command by at least one staff member at the retail location;
transmitting by a retail computer the image and a request for a dental-related product or service to a server over a data communications network, the server forwarding the image and the request to a doctor computer accessible by the licensed dentist;
receiving over the data communications network a message approving or denying the request for the dental-related product or service, the message being transmitted in response to review of the dental-related image by licensed dentist;
displaying the message on a display for prompting the at least one staff member at the retail location to dispense the dental-related product or service from the retail location if the message is a message approving the request for the dental-related product or service, and for prompting the second staff member at the retail location to not dispense the dental-related product or service from the retail location if the message is a message denying the request for the dental-related product or service; and
receiving from the doctor computer over the data communications network identification of a particular type of specialty for referring the customer;
identifying a list of doctors associated with the identified specialty;
transmitting by a server a first notification to at least one doctor in the list;
determining by the server whether a predetermined amount of time has elapsed without a response to the first notification before transmitting a second notification; and
automatically establishing a videoconference session between the requesting computer and a responsive doctor computer accessible by at least one of the doctors in the list.

17. The method of claim 16, wherein the dental-related product or service is a teeth whitening product or service.

18. The method of claim 16, wherein the retail location is in a shopping mall.

19. The method of claim 16, wherein the at least one staff member is a dental assistant.

20. The method of claim 16, wherein the dental-related image is a video image, and the method includes remotely monitoring via an established real-time video transfer session the dispensing of the dental-related product or service.

21. The method of claim 16 further comprising:
providing a plurality of available dental-related products or services, wherein the request for the dental-related product or service is a request for a particular one of the plurality of available dental-related products or services.

22. The method of claim 16, wherein the dental-related product or service is dispensed from the retail location without requiring the customer to visit a dental office to receive the dental-related product or service.

23. A system for dispensing dental-related products or services from a retail site where a licensed dentist is not physically present, the system comprising:
a retail computer transmitting a dental-related image of a customer taken at the retail site by at least one staff member and a request for a dental-related product or service;
a doctor computer accessible by the licensed dentist, the doctor computer receiving the dental-related image and the request, and transmitting a message approving or denying the request for the dental-related product or service in response to review of the dental-related image by the dentist; and
a server coupled to the retail and doctor computers, the server receiving the dental-related image and the request from the retail computer, identifying the licensed dentist in response to receipt of at least the request, and forwarding the dental-related image and the request to the doctor computer, the server further receiving the message transmitted by the doctor computer approving or denying the request for the dental-related product or service and forwarding the message to the retail computer, wherein the retail computer displays the message for prompting the at least one staff member at the retail location to dispense the dental-related product or service if the message is a message approving the request for the dental-related product or service, and for prompting the second staff member at the retail location to not dispense the dental-related product or service from the retail location if the message is a message denying the request for the dental-related product or service, and wherein the doctor computer is configured to transmit over the data communications network identification of a particular type of specialty for referring the customer, and the server is configured to identify a list of doctors associated with the identified specialty, transmit a first notification to at least one doctor in the list, and determine whether a predetermined amount of time has elapsed without a response to the first notification before transmitting a second notification, and wherein the retail computer is configured to automatically establish a videoconference session with a responsive doctor computer accessible by at least one of the doctors in the list.

24. The system of claim 23, wherein the dental-related product or service is a teeth whitening product or service.

25. The system of claim 23 further comprising:
a central database coupled to the server, the central database storing customer files, wherein the server retrieves from the central database a customer file associated with the customer for whom the dental-related product or service is dispensed, and updates the file with the dental-related image.

26. The system of claim 23 further comprising:
a central database coupled to the server, the central database storing referral doctor information, wherein the server searches the central database for information on a referral doctor and transmits the information to the retail computer.

27. The system of claim 23, wherein the retail location is a shopping mall.

28. The system of claim 23, wherein the at least one staff member is a dental assistant.

29. The system of claim 23, wherein the doctor computer is configured to remotely monitor via an established real-time video transfer session the dispensing of the dental-related product or service.

* * * * *